United States Patent
Nichani

[19]
[11] Patent Number: 6,134,343
[45] Date of Patent: *Oct. 17, 2000

[54] SYSTEM OR METHOD FOR DETECTING DEFECT WITHIN A SEMI-OPAQUE ENCLOSURE

[75] Inventor: Sanjay Nichani, Newton, Mass.

[73] Assignee: Cognex Corporation, Natick, Mass.

[ * ] Notice: This patent is subject to a terminal disclaimer.

[21] Appl. No.: 09/287,352

[22] Filed: Apr. 7, 1999

Related U.S. Application Data

[63] Continuation of application No. 08/718,674, Sep. 24, 1996, Pat. No. 5,987,159.

[51] Int. Cl.$^7$ .............................. G06K 9/00; G06K 9/48

[52] U.S. Cl. ..................... 382/141; 382/142; 382/143; 382/199

[58] Field of Search ...................................... 382/141–143, 382/147–149, 176, 194, 270, 294, 224, 180; 348/87, 92, 127; 356/237; 250/223.13, 219, 559.05

[56] References Cited

U.S. PATENT DOCUMENTS

| | | | |
|---|---|---|---|
| 3,739,184 | 6/1973 | Katsumata et al. | 250/223 |
| 4,221,961 | 9/1980 | Payton | 250/223 |
| 4,286,293 | 8/1981 | Jablonowski | 358/199 |
| 4,731,863 | 3/1988 | Sezan et al. | 382/51 |
| 4,876,457 | 10/1989 | Bose | 250/563 |
| 5,054,100 | 10/1991 | Tai | 382/47 |
| 5,153,925 | 10/1992 | Tanioka et al. | 382/52 |
| 5,212,740 | 5/1993 | Paek et al. | 382/22 |
| 5,311,598 | 5/1994 | Bose et al. | 382/8 |
| 5,325,443 | 6/1994 | Beatty et al. | 382/8 |
| 5,436,979 | 7/1995 | Gray et al. | 382/141 |
| 5,481,620 | 1/1996 | Vaidyanathan | 382/169 |
| 5,495,535 | 2/1996 | Smilansky et al. | 382/145 |
| 5,949,901 | 9/1999 | Nichani et al. | 382/149 |
| 5,970,166 | 10/1999 | Nichani | 382/141 |
| 5,987,159 | 11/1999 | Nichani | 382/141 |

OTHER PUBLICATIONS

Automated Vision System for Inspection of IC Pads and Bonds, Sreenivasan et al., *IEEE Transactions on Components, Hybrids, and Manufacturing Technology*, pp. 335–338, vol. 16, No. 3, May 1993.

Discrimination of Planar Shapes Using Matrices, Taza et al. *IEEE Transactions on Systems, Man, and Cybernetics*, pp. 1281–1289, vol. 19, No. 5., Oct. 1989.

Subpixel Image Registration Using Circular Fiducials, Efrat et al., *IEEE*, pp. 49–58, 1993.

Gonzalez et al., Digital Image Processing, Addision–Wesley Company, Inc., 1977, pp. 5–7, and 320–331.

*Primary Examiner*—Jose L. Couso
*Assistant Examiner*—Duy M. Dang
*Attorney, Agent, or Firm*—Anthony L. Miele

[57] ABSTRACT

A method and system detect for the presence of a defect or a non-conforming object of unknown shape, configuration, and location within a semi-opaque enclosure. The semi-opaque enclosure has a pattern which is visible on at least a first of its external surfaces. The semi-opaque enclosure may comprise, for example, a labeled plastic or glass bottle, and the visible pattern may be print and graphical information provided on the bottle's label. A first digital image is captured from first channel light reflected off the first external surface of the enclosure; and a second digital image is captured from second channel light navigating the object inside the enclosure and emanating from the first external surface of the enclosure. A difference image is formed substantially devoid of information representing the visible pattern on the first external surface, by subtracting one of the first and second digital images from the other. Additional segmentation processing may be performed on the difference image in order to better identify the presence of a defect or non-conforming object within the semi-opaque enclosure.

26 Claims, 8 Drawing Sheets

SYSTEM OR METHOD FOR DETECTING DEFECT WITHIN A SEMI-OPAQUE ENCLOSURE

This is a continuation of application Ser. No. 08/718,674 filed Sep. 24, 1996, U.S. Pat. No. 5,987,159.

BACKGROUND OF THE INVENTION

1. RELATED APPLICATION DATA

The present disclosure is related to the following copending, commonly assigned United States patent applications:

U.S. patent application Ser. No. 08/621,189, entitled "Machine Vision Methods for Inspection of Leads on Semiconductor Die Packages," filed in the name of Sanjay Nichani on Mar. 21, 1996;

U.S. patent application Ser. No. 08/621,190 entitled "Machine Vision Methods for Inspection of Semiconductor Die Surfaces," filed in the name of Sanjay Nichani on Mar. 21, 1996;

U.S. patent application Ser. No. 08/621,137, entitled "Machine Vision Methods for Image Segmentation Using Multiple Images," filed in the name of Sanjay Nichani on Mar. 21, 1996; and U.S. patent application Ser. No. 08/716,779, entitled "System or Method for Identifying Contents of a Semi-Opaque Envelope," filed in the name of Sanjay Nichani on even date herewith.

Each of the above-listed copending, commonly-assigned United States patent applications is hereby incorporated herein by reference in its entirety.

2. RESERVATION OF COPYRIGHT

The disclosure of this patent document contains material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

3. FIELD OF THE INVENTION

The present invention relates to a machine vision system or method for detecting at least one object within a semi-opaque enclosure. More particularly, the present invention relates to such a system or method which obtains or enhances an object image while eliminating or diminishing a background image which accompanies the object image.

4. DESCRIPTION OF BACKGROUND INFORMATION

Computer vision, otherwise referred to as image processing, involves the extraction of vision-related information by obtaining signals representing a scene and performing image signal processing on those signals. Applications of computer vision (image processing) techniques include character recognition, industrial inspection of manufactured items, robot guidance systems, radiology, remote sensing, and so on.

Image processing methods may typically comprise several common processing steps, e.g., as described by Rafael C. Gonzalez and Paul White in a book entitled "Digital Image Processing," Addison-Wesley (1992), the content of which is hereby incorporated herein by reference in its entirety.

In a first step, image acquisition is performed to acquire an image of the scene to be analyzed. The image may, for example, be represented in the form of a monochrome or simple digital image f(x,y) discretized both in spatial coordinates x,y and in brightness (gray levels) f.

Pre-processing and enhancement techniques may then be performed on the digital image in order to improve the image and increase the chances for success in subsequent processes. Such pre-processing and image enhancement techniques may include enhancing the contrast between one or more object images and a background image, and filtering noise from the image.

Segmentation may then be performed, which involves distinguishing between different types of regions within the input image, e.g., distinguishing between an object image and a background image.

In a next step, representation and description processing may be performed. In performing representation processing, the data obtained as a result of segmentation is converted into a "representation" suitable for computer processing. In performing description processing, "feature descriptions" are extracted from the representation. Such "feature descriptions" may categorize objects to allow one class of object to be differentiated from another.

In a final stage of the image processing, recognition and interpretation processes are performed. Recognition processing may include assigning a label to an object based upon information provided by its "feature descriptions." Interpretation processing may assign a meaning to an arrangement of recognized objects. For example, several characters may be "interpreted" as forming a particular word.

Golden Template Comparison (GTC) is an image processing method that has been used to detect flaws and defects in two-dimensional scenes of an inspected item which are highly repeatable and do not suffer from geometric distortion. Such scenes are common in semiconductor production and graphic arts applications. Generally, GTC involves the comparison of a test image to an image of a known good scene referred to as a template image. More specifically, the test image is subtracted from the template image, and differences between the two images are observed in order to determine whether a flaw or defect is present within the inspected item.

Generally, GTC comprises two main phases: training and inspection. During training, the template image is constructed by sampling a plurality of images each of which represents a scene of an item absent defects. During inspection, the test image, which represents the scene of the item to be tested (the inspected item), is then compared to the template image. More specifically, the images are subtracted to form a difference image. Thresholding is performed on the difference image to produce a resulting binary image called an error image containing either background (healthy) pixels or defect pixels which represent flaws. The error image is then analyzed in order to determine whether the tested item should be labeled as an "accept" or "fail" item. The analysis that may be performed on the error image may include counting defect pixels found in the error image and performing a blob analysis on the defect pixels. The results of the analysis may be stored in a data structure called a results structure.

A. Issues Concerning the Use of Golden Template Comparison to Inspect the Inner Side-Wall of a Labeled Bottle (1) Changes In Image Intensity In order to produce (with thresholding) an error image which effectively and accurately represents defect pixels separate from healthy pixels, pixels within the difference image must have a sufficiently high gray level value. In order for this to occur, defects must give rise to a change in image intensity in the test image. In graphic arts applications, defects are typically defined in terms of changes in scene reflectivity, which result in a change in image intensity in the test image. Semiconductors are inspected to determine if they contain surface contaminants that can result in a subsequent device failure. Such surface contaminants frequently cause changes in scene reflectivity which thereby change the image intensity of the test image.

In each of these situations, the defect is externally-visible. A problem arises, however, when inspecting semi-opaque enclosures (e.g., when inspecting the inner side-wall of a labeled bottle) to determine whether they contain unwanted objects (defects). In that application, the defect is not externally visible. Therefore, when inspecting the inside of semi-opaque enclosures for defects (non-conforming objects), it is difficult to obtain a test image that exhibits a change in image intensity due to the presence of a defect.

(2) Gray-level Defect Criteria

In order to produce an error image which accurately distinguishes defect pixels from background (healthy) pixels, thresholding may be performed in accordance with appropriate gray-level defect criteria. Various thresholding methods have been proposed which perform thresholding in accordance with different criteria. A simple type of defect criteria is photometric defect criteria which classifies pixels as background (healthy) pixels or defect pixels based upon image intensity alone. Other defect criteria (e.g., based on the shape formed by a group of adjoining defect pixels) can be utilized to guide the thresholding process.

(3) Geometric and Morphological Defect Criteria

The binary error image may be further processed to correct (replace) improperly classified pixels. For example, the binary error image may comprise defect pixels falsely classifying healthy pixels as defects. Accordingly, the binary image may be processed by imposing additional criteria, e.g., based, upon the size and/or shape of a set of adjoining defect pixels. Simply put, defect pixels formed in the error image from small intensity variations in the test image may be ignored (i.e., replaced with healthy pixels) unless they represent a defect which is of a certain size and/or shape (e.g., if the defect is at least several pixels in length or diameter). Geometric and morphological defect criteria are disclosed by William M. Silver and Jean Pierre Schott in a document entitled "Practical Golden Template Comparison," provided by Cognex Corporation, the content of which is hereby incorporated herein by reference in its entirety.

The usefulness of defect criteria (such as geometric and morphological defect criteria) can be significantly diminished when a distorted test image is acquired, e.g., by a conventional bottle inspection arrangement, as shown in FIGS. 7A–7C.

A conventional labeled-bottle visual inspection system is shown in FIG. 7A which comprises a vertically-arranged, elevated camera 200 having a wide-angle lens 200a pointed directly into an upper opening of a bottle 202. Bottle 202 has a semi-opaque label 203 surrounding its outer side-wall surface 210, and is positioned over back lighting 206. A defect 204 is depicted in FIG. 7A with dotted lines, because defect 204 is not visible from outside of bottle 202 due to the opaque nature of label 203. Defect 204 is on an inner side-wall surface 208 of bottle 202, behind label 203. FIG. 7B comprises a cut-away view of bottle 202, in which inner side-wall surface 208 is exposed, and defect 204 is viewable. The view provided in FIG. 7B directly faces defect 204. As depicted, defect 204 is dark in appearance and rectangular in shape.

FIG. 7C shows a 2D test image 201 which is acquired by camera 200 with the use of a wide-angle lens 200a. In order for the complete inner side-wall surface 208 which spans the entire area of label 203 to be inspected, wide-angle lens 200a is used which results in a distorted test image 201. The distorted nature of 2D test image 201 is evident from the relative positions of various portions of bottle 201 within the test image, including lower rim 212 of bottle 202, bottom edge 216 of label 203 and top edge 214 of label 203. The entire area of interest lies between bottom edge 216 and top edge 214.

As shown in FIG. 7C, test image 201 includes a distorted depiction of defect 204. Due to the significant distortion of the shape and size of defect 204 in the 2D test image 201 shown in FIG. 7C, it is difficult to define defect criteria which can be used to accurately identify the existence, size and position of defects. The above-described geometric and morphological defect criteria are not sufficient for this purpose.

(4) Training The Template Image

In performing training, a data structure is created containing information important for the subsequent inspection of a test image. The process includes acquiring several sample images taken under varying conditions, and then calculating statistics from data gathered in connection with the sample images. The calculated statistics include a template image which is the arithmetic mean of the several sample images. The template image is the image which is subtracted from the test image, and may be further used for purposes of normalization mapping. The calculated statistics also include a standard deviation image. This image may be used to derive a threshold image, which may be a linear mapping of the standard deviation image. Other statistics may be calculated from the acquired sample images for purposes of calculating a normalization map. Such statistics may include a histogram, mean, standard deviation, and left and right tails.

The training that is required in Golden Template Comparison is both complicated and time consuming.

(5) Repeatability of Test Image

In addition, in order for the information obtained during training to be useful, the sample images must be highly repeatable (i.e., almost identical in visual appearance) and the 2D test image must not be distorted, e.g., rotated, scaled, or skewed.

These conditions cannot be met when inspecting for defects (or other non-conforming objects) within a semi-opaque enclosure such as a labeled bottle. In the conventional labeled bottle inspection system illustrated in FIGS. 7A–7C, the defect 204 is on an inner side-wall surface 208 of a bottle 202, hidden behind a label 203. Sample images, which would necessarily include an image of label 203, would not be repeatable. This is because the shape of label 203, which forms part of 2D test image 201, changes from bottle to bottle, due to typical variations caused when label 203 is applied to the outer side-wall surface 210 of bottle 203. In addition, 2D test image 201 is clearly distorted due to the use of a wide-angle lens 200a in acquiring the test image.

5. DEFINITIONS OF TERMS

The following term definitions are provided to assist in conveying an understanding of the various exemplary embodiments and features disclosed herein.

Back Lighting:

Lighting produced by a light source (or emanating from a channel) directed toward an image acquisition device such as a camera, and located behind the object of interest. Back lighting causes the image acquisition device to receive a silhouette of the object of interest.

Channel:

A location from which light is emanating. A channel may be a light source or it may be an optical element redirecting light from another light source. Such an optical element may include, for example, a beam splitter, or a split mirror.

Front lighting:

Lighting produced by a light source (or emanating from a channel) directed toward an object of interest and generally on the same side of the object of interest as the image acquisition device.

Segmentation:

A process of distinguishing between different types of regions within an image. Object/background discrimination is a particular type of segmentation which includes identifying those portions within an image corresponding to an object and those portions within the image corresponding to the background. Defect and flaw detection is a type of object/background discrimination.

Training:

A process (commonly used in Golden Template Comparison flaw and defect detection methods) of obtaining a plurality (usually several) sample images of flawless items to generate both a template image and statistical information pertaining to the template image.

SUMMARY OF THE INVENTION

The present invention is provided to improve upon image processing systems and methods for detecting an object within a semi-opaque enclosure. A semi-opaque enclosure is one which is not completely transparent. While objects within the enclosure cannot be seen with the naked eye, light can pass through the enclosure. In order to achieve this end, one or more aspects of the invention may be followed in order to bring about one or more specific objects and advantages, such as those noted below.

One object of the present invention is to provide an improved method for acquiring images and representing those images. The improved method obtains an image accurately representing the object, without distortion, and increases the contrast of the object with respect to a background image accompanying the object image.

Another object of the present invention is to provide an improved segmentation method which can detect a defect (or another object of interest) of unknown shape, configuration, and location from within a semi-opaque enclosure of varying shape and configuration, such as a labeled bottle.

A further object of the present invention is to provide an improved machine vision-based-inspection-system or method which facilitates an accurate interpretation of inspection results. More specifically, the machine vision-based inspection system or method detects defects with high sensitivity but with a decreased occurrence of false alarms, i.e., false "failure" indications.

Other features may be provided to achieve yet additional objects and advantages. For example, a simplified template comparison segmentation technique may be provided which detects flaws and defects in a semi-opaque enclosure such as a labeled bottle. The simplified template comparison technique does not require high repeatability of the items being inspected; that is, the technique does not require that each item be identical. The simplified technique is thus appropriate for accurately detecting defects present on inner side-wall surfaces of labeled bottles or other defects within other types of semi-opaque enclosures.

The simplified template comparison technique does not require training as do Golden Template Comparison and similar techniques. A template image is obtained almost simultaneously with the obtaining of the test image. More specifically, the template image is "dynamic" and corresponds precisely to the particular item being inspected at that moment.

The present invention, therefore, is directed to a method or system for detecting the presence of a defect or non-conforming object (at least one) of unknown shape, configuration, and location within a semi-opaque enclosure. The semi-opaque enclosure may comprise a labeled plastic or glass bottle.

The semi-opaque enclosure has at least first and second external surfaces, where the first external surface has a pattern visible externally to the enclosure (e.g., print and graphical information provided on a bottle label).

A first digital image is captured from first channel light reflected off the first external surface of the semi-opaque enclosure. More specifically, the first digital image may be a reflected-light image formed with front lighting impinging on a front side of the rigid semi-opaque enclosure. A second digital image is captured from second channel light navigating the object inside the enclosure and emanating from the first external surface of the enclosure. More specifically, the second digital image may be a transmitted-light image formed with back lighting, which is directed onto a back side of the semi-opaque enclosure and thus forms a silhouette image of the object inside the enclosure. The silhouette image emanates from the first external surface (e.g., the front side) of the enclosure. A difference image is formed substantially devoid of information representing the visible pattern on the first external surface, by subtracting one of the first and second digital images from the other.

BRIEF DESCRIPTION OF THE DRAWINGS

The above and other objects, features and advantages of the present invention are further described in the detailed description which follows, with reference to the drawings by way of non-limiting exemplary embodiments of the present invention, wherein like reference numerals represent similar parts of the present invention throughout the several views, and wherein.

DETAILED DESCRIPTION OF THE EXEMPLARY EMBODIMENTS

The present invention is directed to a system or method for using electromagnetic radiation, more specifically—light (e.g., visible light having a wavelength between 400 nm–760 nm), in a particular manner to separate out different aspects of an image, causing an object (at least one) to stand out in relation to the background within the image. The object may be located within a semi-opaque enclosure. Two separate images are formed using at least two separate light channels. One of the light channels emphasizes the object in relation to a background image, while the other light channel either de-emphasizes the background image or causes the background image to remain the same in relation to the object image. In any event, the background image is present in both the first and second separate images. Thus, one image may be subtracted from the other, causing the background image to be subtracted out and the object image to remain.

This may be achieved, in certain industrial applications, using grazing light and on-axis light, for example, as disclosed in the above-identified U.S. patent application entitled "Machine Vision Methods for Image Segmentation Using Multiple Images," (Attorney Docket No. 150448-030). An alternate method may be used to detect (and, if desired, also identify or categorize) objects located within a semi-opaque enclosure, such as a labeled bottle or a paper envelope. A first digital image may be captured from first channel light (front lighting) reflected off a front external surface of the semi-opaque enclosure; and a second digital image may be captured from second channel light (backlighting) which navigates the object inside the enclosure and emanates from the front external surface of the enclosure.

A difference image may then be formed which is substantially devoid of information representing the visible pattern provided on the front external surface of the enclosure, by subtracting one of the first and second digital images from the other. This occurs since both the first digital image (i.e., the reflected-light image) and the second digital image (i.e., the transmitted-light image) each contain the background image, while only the second digital image (the transmitted-light image) contains the object to be detected. Thus, when one of the images is subtracted from the other, the background information is subtracted out, leaving only an image representing the object.

Figure 1:
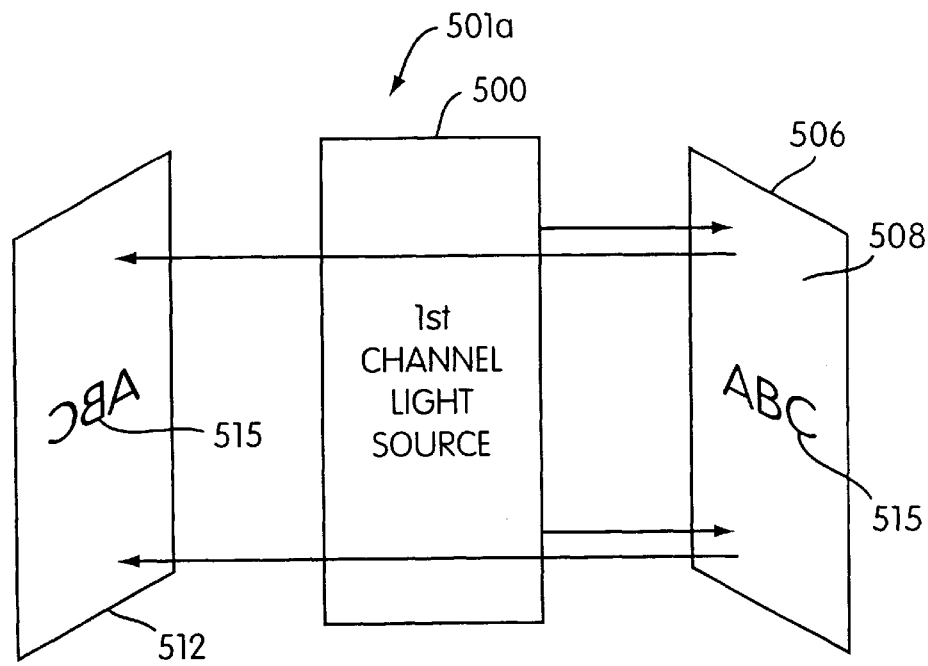
FIGS. 1 and 2 show respective image acquisition subsystems for generating a reflected-light image and a transmitted-light image.
Figure 2:
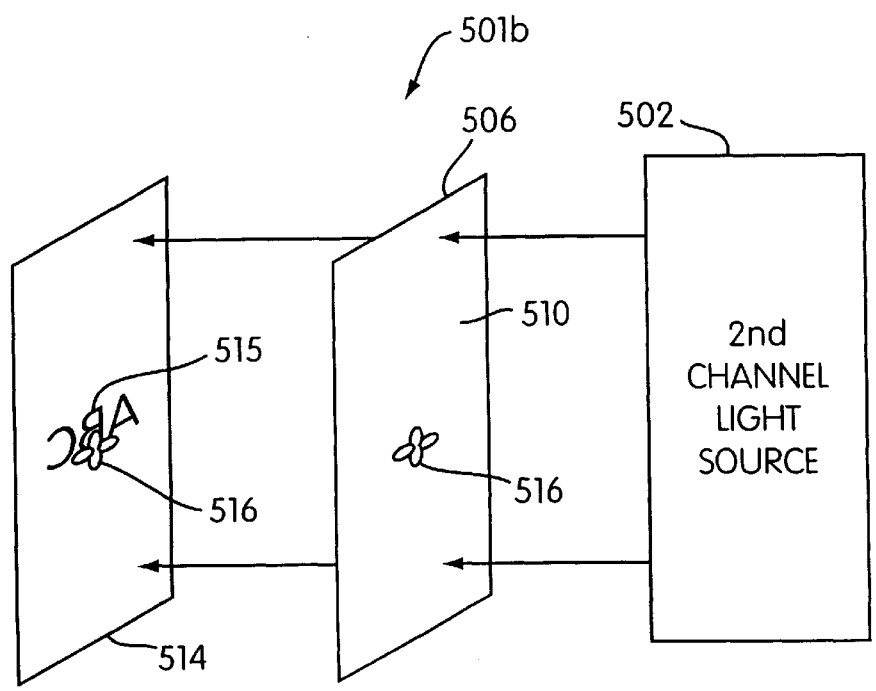

FIG. 1 illustrates a reflected-light subsystem (first image acquisition subsystem) 501*a*, and FIG. 2 illustrates a transmitted-light subsystem (second image acquisition subsystem) 501*b*. In FIG. 1, first channel light, referred to in FIG. 1 as a first channel light source 500, is provided which shines light toward a front surface 508 of an item 506.

Item 506 comprises part of a complete semi-opaque enclosure, such as an envelope or a labeled bottle, or another type of semi-opaque enclosure which may contain an object or a defect that is to be detected. In FIGS. 1 and 2, item 506 is a portion of an outer side wall of a labeled bottle; remaining portions of the labeled bottle have been omitted to simplify the explanation of the features depicted. The illustrated label includes the letters "ABC" printed on its outer front surface 508.

First channel light source 500 comprises front lighting, which is directed toward front surface 508 of enclosure 506. As shown in FIG. 1, first channel light source 500 is provided on the same side of enclosure 506 as an imaging surface upon which a reflected-light image 512 is formed. Light is reflected from front surface 508 back toward the imaging surface to form reflected-light image 512. The reflected-light image 512 includes print 515 which is visible externally to enclosure 506 and is located on front surface 508.

In FIG. 2, a second channel light source 502 is provided which serves as back lighting. Second channel light source 502 is directed toward an imaging surface (upon which transmitted-light image 514 is formed), but is located behind enclosure 506. In other words, item 506 is located between second channel light source 502 and the formed transmitted-light image 514. Light from second channel light source 502 is shined onto an inner surface 510 of item 506 (which is a front wall of the enclosure), traversing an object to be detected 516 (which is opaque, and, in this case, comprises a winged insect) inside the enclosure and emanating from the front external surface 508 of the enclosure, eventually arriving at an image plane upon which a transmitted-light image 514 is formed. Transmitted-light image 514 includes a reverse image of both alphanumeric characters "ABC" 515, which form a background image, as well as object 516.

Figure 3A:
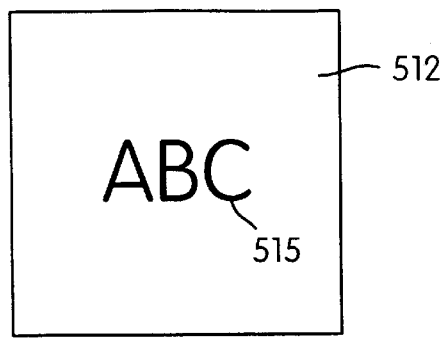
FIG. 3A illustrates a reflected-light image generated by the subsystem illustrated in FIG. 1.
Figure 3B:
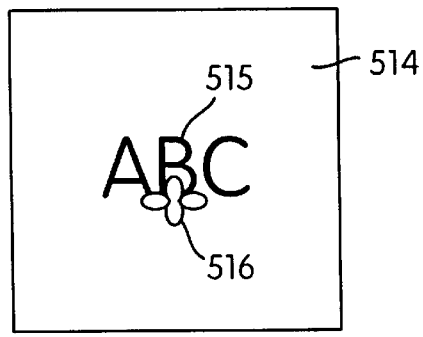
FIG. 3B illustrates a transmitted-light image generated by the subsystem illustrated in FIG. 2.
Figure 3C:
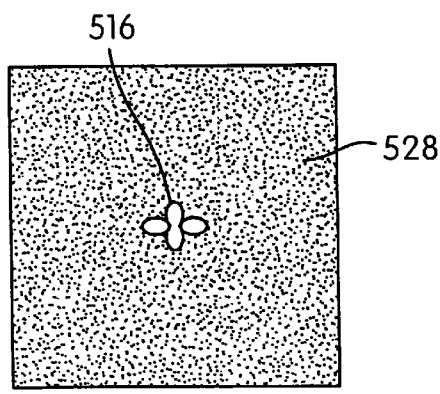
FIG. 3C represents a gray-level difference image produced by subtracting the image of FIG. 3B from the image of FIG. 3A.

FIG. 3A illustrates reflected-light image 512, and FIG. 3B illustrates transmitted-light image 514. As can be seen in FIGS. 3A and 3B, each of these images includes the same background information, representing background print 515, while only transmitted-light image 514 includes an image of object 516. A difference image is shown in FIG. 3C. When one of the images shown in FIGS. 3A and 3B is subtracted from the other, the background information is removed, and only object 516 remains. Thresholding is performed on the gray-level difference image 528 shown in FIG. 3C, which causes a binarized image to be produced. Thresholding techniques that may be used will be further described below. A segmented binary image is thus produced that includes an accurate depiction of detected object 516. The binary image may contain a matrix of pixels, with defect pixels (e.g., "1's") representing detected object 516, and background (healthy) pixels (e.g., "0's") representing background information.

Figure 4:
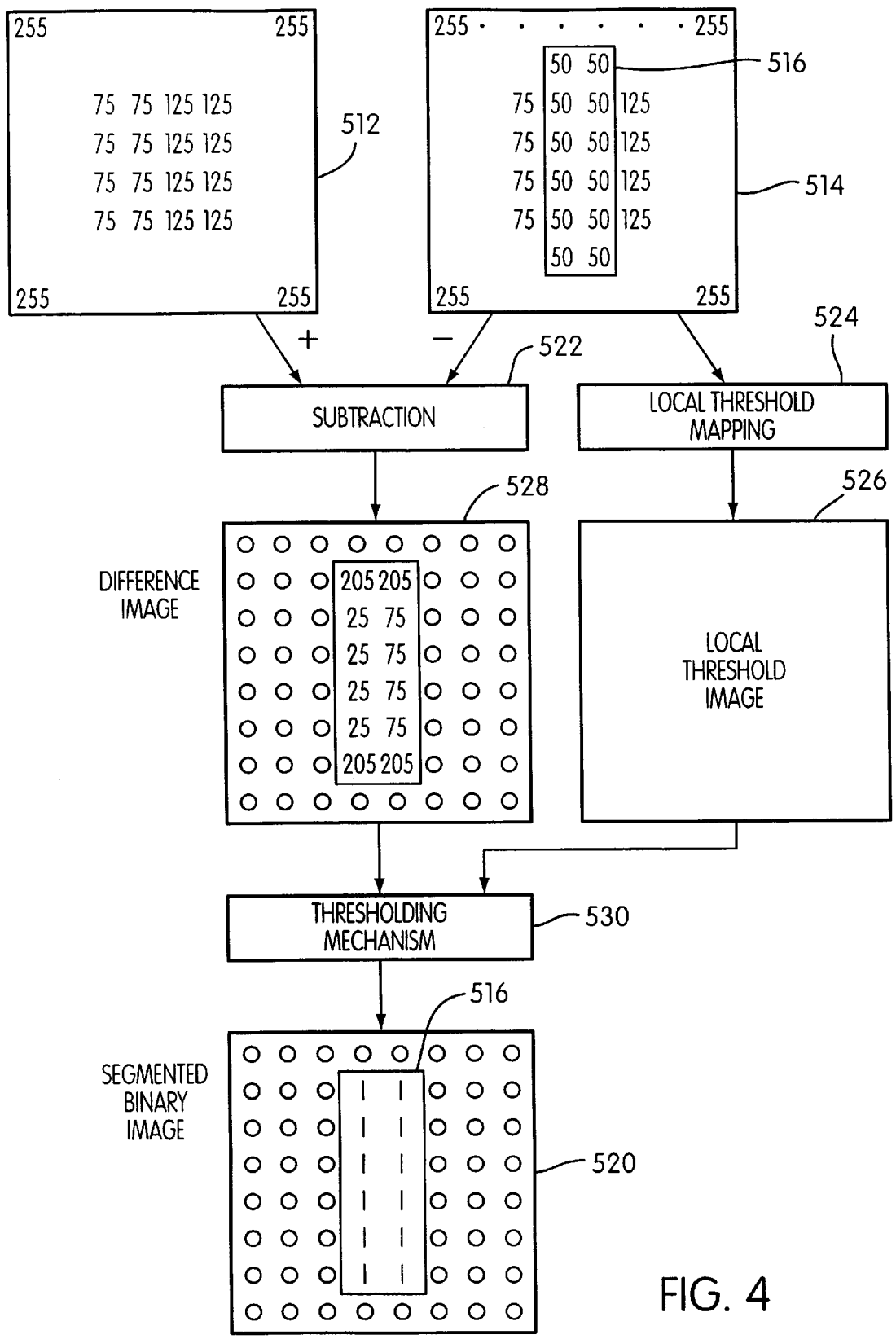
FIG. 4 illustrates a segmentation process being performed on a simplified exemplary digitized gray-level image (having 8×8 pixels)

FIG. 4 is a diagram depicting simplified exemplary first and second gray-level digital images, including reflected-light image 512 and transmitted-light image 514 (each with 8×8 pixel images, and simplified background and object information). In FIG. 4, reflected-light image 514 includes only background information, including a white perimeter represented by high pixel (gray-level) values of 255 and a pattern at a center location represented by lower pixel (gray-level) values of either 75 or 125. Transmitted-light image 514 includes a significant portion of the background information contained in reflected-light image 512, but also includes gray-level values depicting a detected object 516.

When transmitted-light image 514 is subtracted from reflected-light image 512 (or vice versa), the differences between the low/dark gray-level values of object 516 and the lower/darker gray-level values corresponding to the background pattern become small (and thus result in small gray-level values in the corresponding pixels of difference image 528). More specifically, in the illustrated example, when 50 is subtracted from 75, at certain locations corresponding to object 516, difference image 528 will comprise pixels with lower gray-level values of 25. At other locations within object 516, the difference image will include higher gray-level values of 75. Where there is no overlap between object 516 and the background patterns, a largest resulting gray-level value is produced in difference image 528, that value being 205.

If a single threshold value is used to binarize difference image 528, errors will likely occur in the resulting segmented binary image 520. That is, the resulting binary image 520 would not likely represent an accurate segmentation. For example, if a single threshold value is set to a high value, for example, a value greater than 25, then the resulting segmented binary image 520 would include a number of broken/disjointed regions, i.e., regions within object 516 which would be inaccurately identified as part of the background. This would hinder the ability to identify object 516, or otherwise recognize it as a defect. If a single threshold value is set to a low value, then the system is susceptible to picking up shadows and other noise which are part of the background image and not part of object 516. Such shadows and noise can cause the apparent shape of object 516, as depicted in the resulting segmented binary image 520, to become distorted.

In order to address these problems, a local thresholding technique may be provided. Accordingly, as shown in FIG. 4, a local threshold mapping step, or mechanism, 524 may be provided for producing a local threshold image 526. That local threshold image 526 can then be used to control a thresholding mechanism 530. Thresholding mechanism 530 may then apply different threshold values to the respective corresponding pixels of gray-level difference image 528 in order to obtain a segmented binary image 520 that accurately depicts the size, location, and shape of object 516.

The illustrated local threshold image 526 is formed as a function of transmitted-light image 514. In the alternative, it may be formed as a function of reflected-light image 512, or as a function of both transmitted-light image 514 and reflected-light image 512. Local threshold image 526 contains a number of pixels corresponding to each of the pixels of difference image 528, and each pixel value of local threshold image 526 is set to a value chosen to prevent thresholding mechanism 530 from (1) disrupting or disjointing regions within object 516, and (2) including shadows and other noise in the resulting segmented binary image 520.

Reflected-light image 512 may be referred to as a first digital image, while transmitted-light image 514 may be referred to as a second digital image. The first and second digital images may comprise two-dimensional gray-level images represented with respective two-dimensional light intensity functions $f_1(x,y)$ and $f_2(x,y)$, wherein x and y denote spatial coordinates and $f_1$ and $f_2$ are values proportional to the brightness (gray-level) of the respective image at a point x,y.

Pre-processing and enhancement techniques may be performed on the first and second digital images in order to improve those images and increase the chances for success in subsequent processes. As shown in FIG. 4, such an image enhancement technique may comprise subtracting one of the first and second digital images from the other in order to form a two-dimensional gray-level difference image 528. Specifically, the second digital image 514 may be subtracted from first digital image 512 with use of a subtraction mechanism 522.

Subsequent to performing the pre-processing and enhancement techniques on the first and second digital images acquired based upon the scene to be analyzed, a resegmentation operation may be performed on the difference image in order to form a two-dimensional binary (two-level) image from the difference image. Such a resegmentation operation may comprise a thresholding operation performed on the difference image d(x,y), to form a two-dimensional binary thresholded image g(x,y). As noted above, problems may arise if a single static global threshold value is used, including disruption and disjoining of regions within object 516, or shadows and other noise in the resulting segmented binary image. Therefore, a single static global threshold may present severe limitations on the quality of the resulting segmented binary image.

Preferably, a threshold function T is used which uses different threshold values for different pixels within the difference image d(x,y). Let p(x,y) be a threshold image. The resulting two-dimensional binary thresholded image g(x,y) may be defined as equal to "1" if d(x,y) is greater than p(x,y), and "0" if d(x,y) is less than or equal to p(x,y). x and y represent spatial coordinates of a pixel (x,y) of the difference image, d(x,y) is the gray-level of the pixel (x,y) and p(x,y) is a local threshold control variable corresponding to the pixel (x,y).

p(x,y) may represent a gray-level local threshold image defined as a function of at least one of the first and second digital images $f_1(x,y)$ and $f_2(x,y)$. p(x,y) may be obtained by performing a local threshold mapping operation on the second digital image $f_2(x,y)$. The local threshold mapping operation may comprise performing point processing in the spatial domain on the second digital image $f_2(x,y)$ in accordance with r=dmap(s), for a pixel having spatial coordinates (x,y) where dmap is a mapping function, r is a gray-level equal to p(x,y) and s is a gray-level equal to $f_2(x,y)$.

The function r(s) may be defined in accordance with its slope. More specifically, the slope of r(s) may be defined to continuously increase as the value of s increases. In the specific embodiment illustrated herein, r is defined as follows:

$r=s^2 t/1000$, where t is a threshold coefficient which may be determined empirically.

Referring back to FIG. 4, once local threshold image 526 is obtained, thresholding mechanism 530 subtracts it from difference image 528. Thresholding mechanism 530 then binarizes the result using a map, such that pixels with positive difference values are replaced with a defect pixel (e.g., a "1") and pixels with a negative difference value are replaced with a background (healthy) pixel (e.g., a "0"). An exemplary resulting segmented binary image 520 is illustrated at the bottom of FIG. 4.

Other mapping functions may be performed which form a specific local threshold image as a function of one, the. other, or both of reflected-light image 512 and transmitted-light image 514, in order to compensate for variations in the gray-levels (due to object 516) within gray-level difference image 528.

Figure 5:
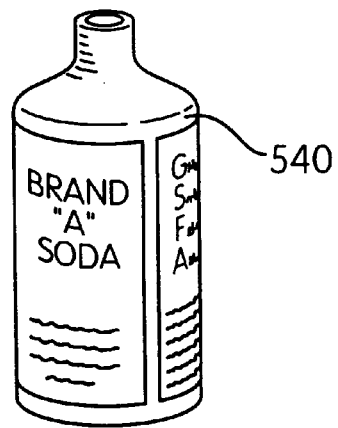
FIG. 5 is a perspective view of a soda bottle with a label surrounding its outer side wall.

FIG. 5 is a perspective view of a bottle having a brand "A" soda label surrounding the bottle's periphery, attached to an outer surface of the bottle's side wall. A computer vision system may be utilized to detect whether an item located inside a semi-opaque enclosure, such as bottle 540, and (if desired) to identify the detected item. In the specific case of bottle 540, a soda company may wish to inspect the inside surface of bottle 540 to determine whether it contains any unwanted debris or matter. The semi-opaque enclosure (a labeled bottle 540 as shown in FIG. 5) allows visible light to pass through from one side of the enclosure to the other and to be detected by an image acquisition device such as a CCD (Charged Coupled Device). Accordingly, a reflected-light image and a transmitted-light image may each be obtained and utilized to detect (and optionally also identify) an item located within the semi-opaque enclosure.

Figure 6A:
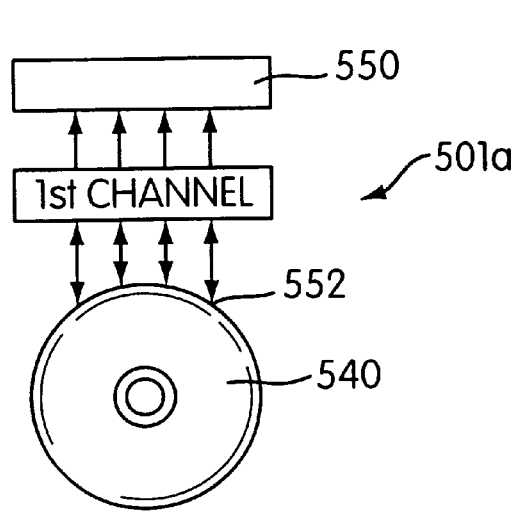
FIGS. 6A and 6B respectively illustrate a reflected-light subsystem and a transmitted-light subsystem.
Figure 6B:
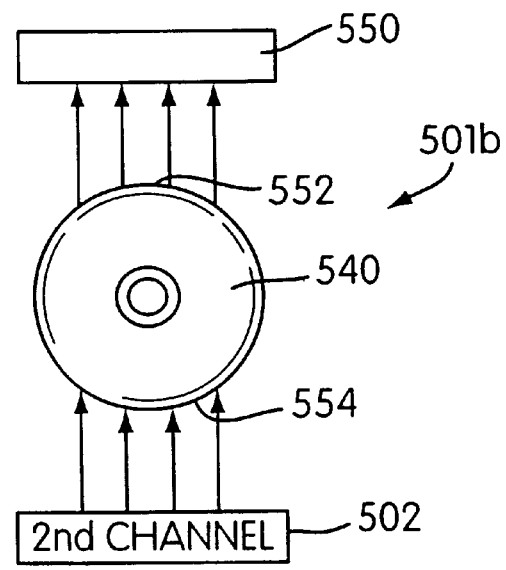
Figure 7A:
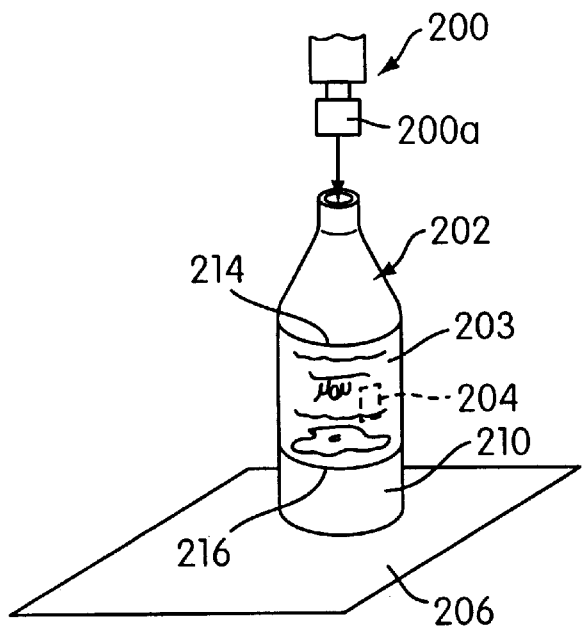
FIG. 7A illustrates a conventional labeled-bottle visual inspection system.
Figure 7B:
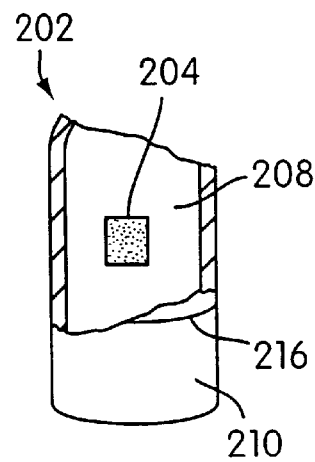
FIG. 7B is a cut-away view of the bottle illustrated in FIG. 7A.
Figure 7C:
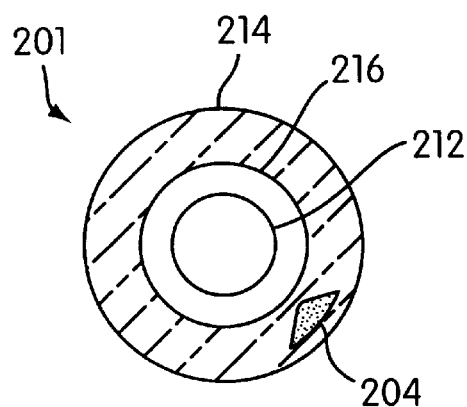
FIG. 7C depicts a 2D test image formed using the conventional labeled-bottle visual inspection system of FIG. 7A.

FIGS. 6A and 6B respectively illustrate a reflected-light subsystem (a first image acquisition subsystem) 501a and a transmitted-light subsystem (a second image acquisition subsystem) 501b. In FIG. 6A, light originates from a first channel source 500 and is reflected off a front surface 552 of bottle 540. The reflected light then impinges upon an image plane provided within image acquisition device 550. In FIG. 6B, a second channel source 502 produces second light, significantly brighter than the first light produced by first channel source 500. The second light is directed onto a back surface 554 of bottle 540. The second light produced by second channel source 502 comprises back lighting, while the first light produced by first channel light source 500 comprises front lighting. The back lighting should be significantly brighter than the front lighting, since a significant amount of the back lighting (the second light) will be lost as it is transmitted through bottle 540 before it exits front surface 552 of bottle 540 and impinges upon the image plane provided within image acquisition 550.

Referring to the transmitted-light subsystem 501b, the second light impinging upon the image plane of image acquisition device 550 includes print information derived from front surface 552 of bottle 540, but does not include print information and other visible features which may be on the back surface 554 of bottle 540. This is because the light that impinges upon back surface 554 is deflected and dispersed within the inside of bottle 540, and, therefore, information concerning features on back surface 554 does not reach the image plane of the image acquisition device 550.

In FIG. 6A, the first light originates from first channel source 500 and impinges upon a front surface 552 of bottle 540. The first light is reflected directly back toward an image plane provided within image acquisition device 550. The resulting reflected-light image also contains the print which is on front surface 552 of bottle 540, as does the transmitted-light image. That print will form part of the background information which will be subtracted out.

Figure 8:
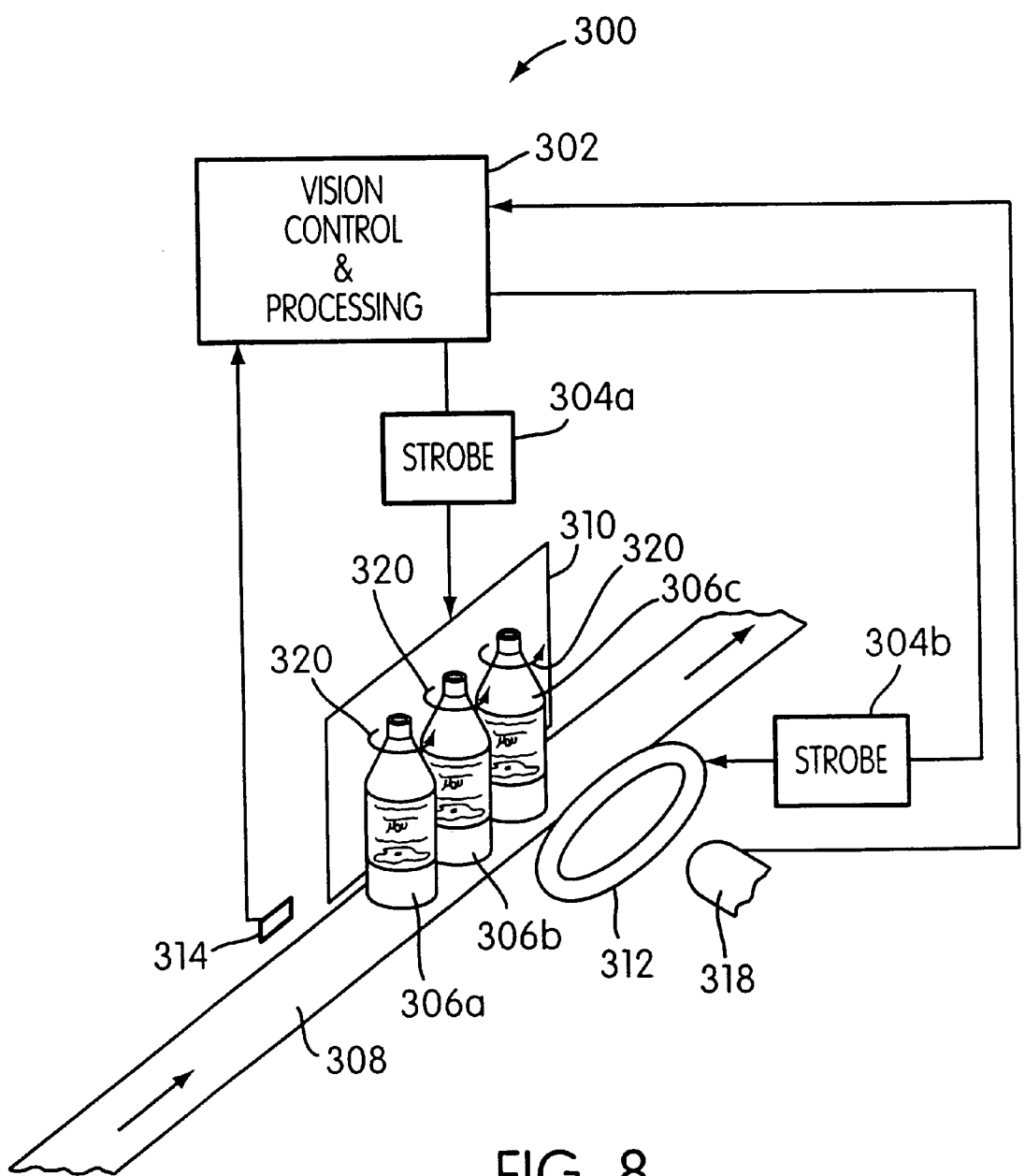
FIG. 8 is a perspective view of an illustrative embodiment of a labeled-bottle visual inspection system which may be provided in connection with the present invention.

FIG. 8 is a perspective view of a labeled-bottle visual inspection system 300. The illustrated system 300 comprises a vision control and processing computer system 302, an ensemble of bottles 306x (including the bottles 306a–306c shown in FIG. 8 and others (not shown)) supported by a conveyor 308, and various image acquisition components. A front light 312 is positioned in alignment with a vertical plane which is parallel to the direction of movement of conveyor 308.

A back light 310 is positioned in alignment with a vertical plane which is also parallel to the direction of movement of conveyor 308. Front light 312 is positioned in front of, and at a corresponding height with, a three-bottle set 306a–306c. Back light 310 is also positioned at the is same height, behind the three-bottle set. Accordingly, bottles 306a–306c are positioned directly between front light 312 and back light 310.

The image acquisition components further comprise a camera 318, a plurality of strobes 304a, 304b, and a position sensor 314.

As the ensemble of bottles 306x (including the three-bottle set 306a–306c, positioned between back light 310 and front light 312) moves along conveyor 308, transmitted-light and reflected-light images are obtained of the selected three-bottle set, each time the bottles are moved along conveyor 308 by a distance corresponding to one bottle. The table below illustrates the manner in which the necessary images can be obtained in order to inspect the complete inside and outside of each bottle. The illustrated labeled bottle inspection system 300 is capable of inspecting the complete insides of the bottles, including portions which are covered by a semi-opaque label, and is further capable of inspecting the outside surfaces of the bottles. In order to do this, three sets of images are taken for each bottle. A first set of reflected-light and transmitted-light (first and second) digital images may be obtained while a bottle is in a first orientation (rotated by 0°), a second set of such images may be obtained while the same bottle is in a second orientation (rotated by 120°), and a third set of such images may be obtained while the bottle is in a third orientation (rotated by 240°).

|  | Position One | Position Two | Position Three | Orientation |
| --- | --- | --- | --- | --- |
| $t_1$ | b3 | b2 | b1 | 0° |
| $t_2$ | b4 | b3 | b2 | 120° |
| $t_3$ | b5 | b4 | b3 | 240° |

As shown by the above table, a bottle b3 enters the range of the image acquisition system at position 1 at a time $t_1$. At that time, the orientation of bottle b3 is 0°. Then, at time $t_2$, bottle b3 is moved to position 2 which corresponds to a center location within the viewable range of the image acquisition system. At that location and time, the orientation of bottle b3 is 120°. Then, at time $t_3$, bottle b3 is again incremented to correspond now to position 3 which is the right-most position within the range of the image acquisition system. At this position and time, the orientation of bottle b3 is 240°.

When a three-bottle set is within the range of the image acquisition system, including front light 312, back light 310, and camera 318, a total reflected-light image (first digital image) is obtained which includes an image of the entire profile of all three bottles within the three-bottle set. Similarly, the transmitted-light image (second digital image) includes the complete profile of all three bottles within the three-bottle set. Conventional inspection processing methods may be performed to determine whether defects exist on the outer surfaces of the bottles. Similarly, in order to inspect the inner side-wall surfaces of the bottles at locations corresponding to transparent portions of the bottles (i.e., portions of the bottles not corresponding to the semi-opaque labels), conventional inspection processing methods may be performed.

In order to inspect for defects and non-conforming objects located behind a semi-opaque label, the pertinent portions of the overall bottle image (i.e., the pertinent portions of the first (reflected-light) digital image and second (transmitted-light) digital image) are obtained before subsequent processing is performed.

Sensor 314 is utilized to generate a signal when the position of a bottle corresponds to sensor 314 as it is moved by conveyor 308. Vision control and processing computer system 302 determines when a certain amount of time passes from the point at which the bottle passes sensor 314, in order to determine when a three-bottle set 306a–306c is in correct alignment with the image acquisition system. Accordingly, vision control and processing computer-system 302 facilitates registration of three-bottle sets with the image acquisition system.

The rotation of each of the bottles may be effected with an appropriate mechanical mechanism such as a belt mechanism conventionally provided in industrial settings in which bottles are mass-produced, mass-assembled, and/or mass-processed. Such a rotating mechanism is illustrated schematically with arrows 320 in FIG. 8.

The system illustrated in FIG. 8 may be modified and still facilitate thorough inspection of the inner side-wall surfaces of labeled bottles. For example, one or more cameras may be provided to capture first and second images, the bottles may be moved in a different manner, and may be rotated through less orientations. For example, two sets of images may be obtained for each bottle, by rotating a bottle from a first orientation (at 0°) to a second orientation (rotated by 90°). In addition, different lighting and/or mirror arrangements may be provided to effect the front and back lighting needed to produce the transmitted-light and reflected-light images.

Strobes 304a and 304b are provided to freeze the motion in the obtained images. They are controlled to correspond in time with the taking of the images by camera 318. This is done in order to prevent blurring in the resulting captured images. Movement of a bottle by an amount equivalent to one-half or more pixels can significantly blur the captured image. Bottles are typically moved in industrial settings at a fast pace, usually at 600 bottles per minute. Therefore, it is very important to take steps to prevent blurring of the captured images used for inspection. An additional, or alternate, measure that can be taken to reduce or eliminate blur is use of a shutter camera, which will localize (in time) the visual information which is used to capture each image.

Sensor 314 may comprise a transmittive or a reflective light-based sensor or another type of sensor which can accurately generate a signal indicating the physical presence and position of a bottle for use by vision control and processing computer system 302.

Diffused and/or parallel beam light sources may be used to produce either or both the front lighting and back lighting. In the embodiment illustrated in FIG. 8, front light 312 comprises a ring light which may be a commercially available FOSTEC brand 5" ring light. In the alternative, another type of diffused light or collimated light can be used to produce the front lighting for the system in FIG. 8. A beam splitter or a split mirror may be used so that the front lighting does not interfere with the optical axis of camera 318.

In the embodiment illustrated in FIG. 8, back light 310 may comprise a commercially available FOSTEC brand back light. Similarly, the back light may be implemented with other types of light sources, including a diffused light and/or collimated light. Multiple line lights can be used to form the back lighting. Multiple point lights and/or multiple fiber optic bundles may be used to form the back lighting as well.

Figure 9:
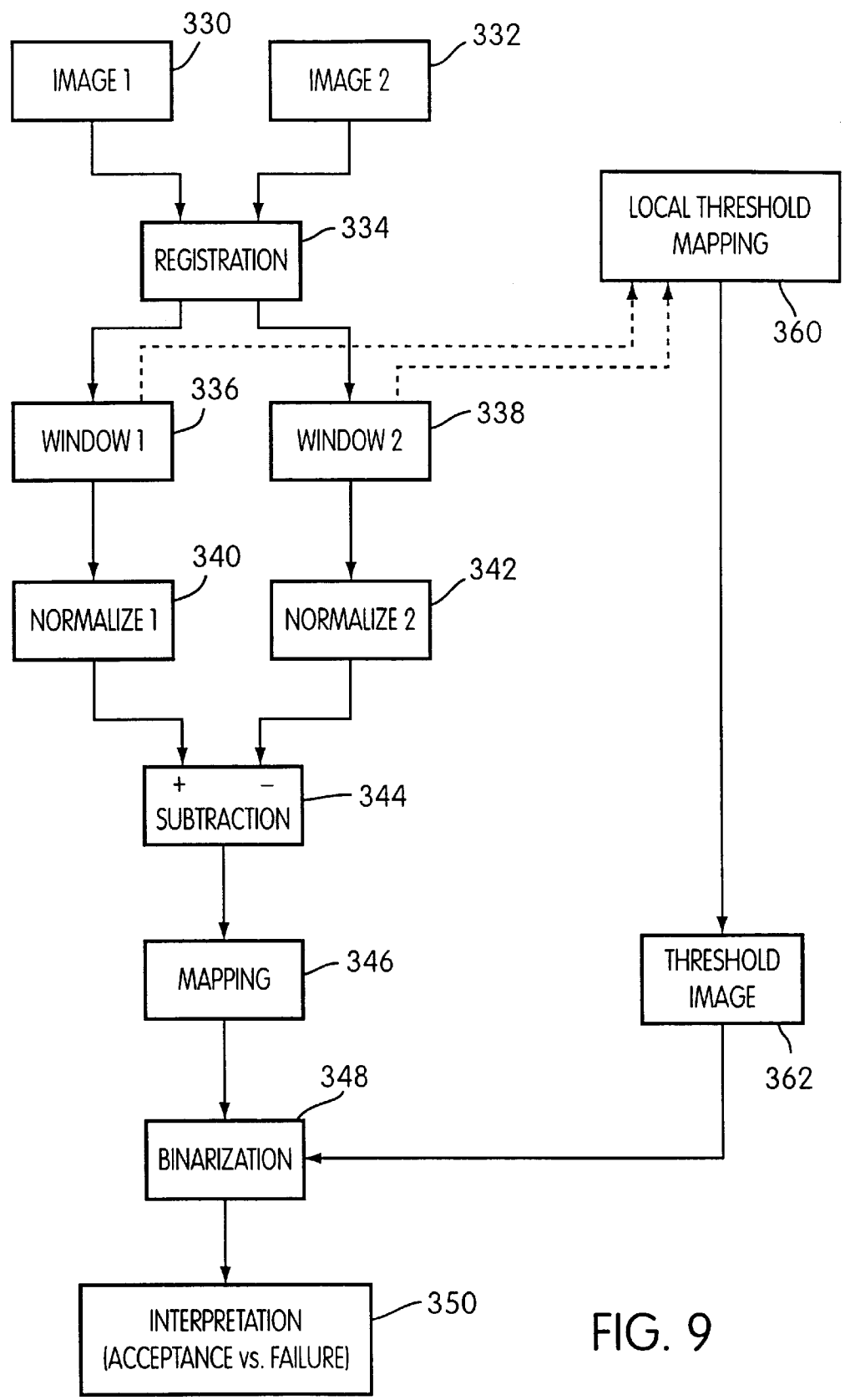
FIG. 9 is a flow chart illustrating a visual inspection process which may be performed in connection with the visual inspection system shown in FIG. 8.

FIG. 9 is a flow chart of the image processing which may be performed in connection with the visual inspection system illustrated in FIG. 8. A first digital image 330 and a second digital image 332 are each obtained for each orientation of each bottle. A registration mechanism 334 is provided to digitally register first digital image 330 with second digital image 332. Registration mechanism may perform such digital registration in accordance with a method utilizing two-dimensional cross-correlation of images as is disclosed by Jain in chapter 2 of a book entitled "Fundamentals of Digital Image Processing," Prentise Hall (1989). Chapter two of that book is hereby incorporated herein by reference in its entirety. Other additional or alternative digital registration techniques may be used at this point of image processing as well.

The registered images are then forwarded to first and second windows 336 and 338. First and second windows 336 and 338 obtain appropriate portions of the overall first and second digital images 330 and 332, for subsequent processing. When inspecting a labeled bottle, as illustrated in FIG. 8, the portion of the image obtained by the first and second windows 336 and 338 corresponds to the portion of bottle covered by a label. After windowing the first and second digital images with first and second windows 336 and 338, the resulting gray-level windowed first and second digital images may be normalized by first and second normalization mechanisms 340 and 342.

Normalization may be performed on one or both of the first and second digital images output by first and second windows 336 and 338. Normalization is performed on the first and second test images to compensate for normal changes or differences in lighting and aperture between the two images. Normalization is performed in Golden Template Comparison for similar reasons in order to compensate for normal changes in lighting between a test image verses a template image.

Normalization may be performed by pixel mapping in order to transform gray-scale values to another set of values. Such a pixel map may be derived using statistics based upon one or both of the windowed first and second digital images. More specifically, by way of example, a pixel map may be derived based upon one or both of the windowed images, from histogram equalization, mean and standard deviation, tail matching, or identity transformation. With histogram equalization, a pixel map is derived from a histogram of a digital image. Using the mean and standard deviation, such a pixel map may be derived using the mean and standard deviation calculated from a digital image. In tail matching, mapping is performed in accordance with left and right tails, which are outlying points (representing gray-scale values) on the left and right ends of a histogram, beyond which gray-scale values are considered unreliable. The gray-scale values lying outside of these tails are discarded before mapping is performed. In order to normalize the first windowed digital image with respect to the second windowed digital image, the range of gray-scale values between the tails of one of the image's histogram may be linearly mapped to correspond to the range between the tails of the histogram of the other of the two images. With identity transformation, each gray-scale value of the image is mapped to itself; i.e., there is no change in the image.

Once normalization (if necessary) is performed by one or both of first and second normalization mechanisms 340 and 342, the windowed second digital image is subtracted from the windowed first digital image with the use of a subtraction mechanism 344. The result of subtraction produces a difference image d(x,y). The difference image d(x,y) is then mapped with the use of a mapping mechanism 346. At this stage of the processing, mapping may comprise linear mapping of the various pixel values within difference image d(x,y) to remove any negative pixel values present in the difference image as a result of the subtraction. Accordingly, a single value may be added to each of the pixel values within the difference image to eliminate any negative pixel values. Normalization may also be performed by the mapping mechanism 346 in order to normalize and/or rescale the difference image to facilitate later stages of processing.

The processing performed by first and second normalization mechanisms 340 and 342, subtraction mechanism 344, and mapping mechanism 346 comprise image enhancement techniques. Subtraction mechanism 344 performs a preliminary stage segmentation, facilitating object/background discrimination based upon windowed first and second digital images $f_1(x,y)$ and $f_2(x,y)$.

Subsequent to the image enhancement techniques, a subsequent-stage segmentation is performed by binarization mechanism 348. More specifically, the mapped normalized gray-level difference image output by mapping mechanism 346 is resegmented (binarized). This binarization is performed in accordance with a threshold image 362, which may be defined by a local threshold mapping mechanism 360 produced in accordance with local threshold mapping as described previously.

Upon receipt of a binarized error image output by binarization mechanism 348, an interpretation mechanism 350 analyzes the various defect pixels in relation to background (healthy) pixels in order to determine whether the inspected item should be categorized as either an acceptance or a failure item. The interpretation processing may be implemented by simply counting the number of defect pixels present in the error image and/or by utilizing Blob analysis. These techniques are well-known in the art, and therefore are not discussed in detail herein.

Figure 10:
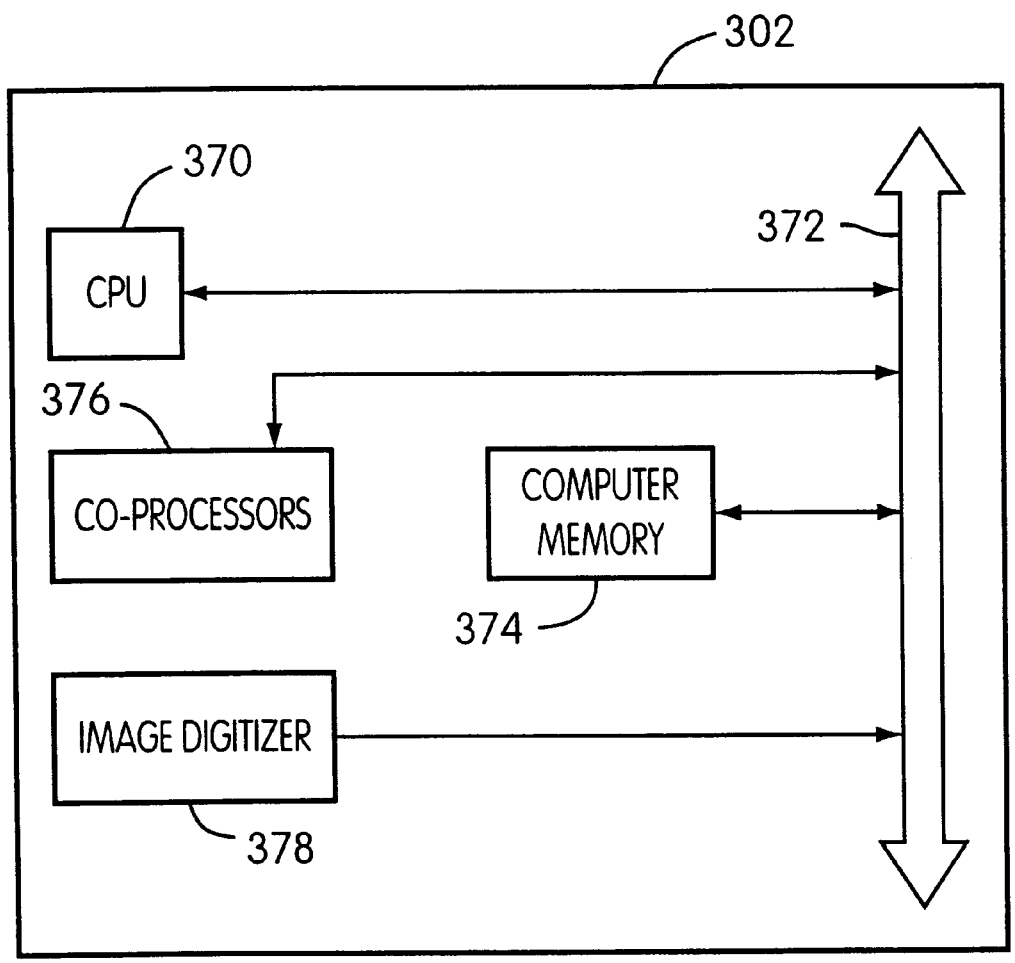
FIG. 10 is a block diagram of a system which may be used to carry out the functions of the vision control and processing computer system depicted in FIG. 8.

FIG. 10 is a block diagram of several devices which may be used to carry out the functions of visual control and processing computer system 302 depicted in FIG. 8. Vision control and processing computer system 302 may control the operation of conveyor 308, sensor 314, as well as the strobes and light sources of the system shown in FIG. 8. Vision control and processing computer system 302 may also control the operation of rotation mechanisms 320 and camera 318. Vision control and processing computer system 302 may also perform the various processes depicted in FIG. 9.

In order to perform some or all of these functions, as illustrated in FIG. 10, vision control and processing computer system 302 may be provided with a central processing unit 370, together with a bus structure 372 and a computer memory 374. In order to increase the speed of processing, co-processors 376 may be provided. Vision control and processing computer system 302 may also comprise an image digitizer 378 for digitizing images. This additional feature can also significantly increase the speed and efficiency of the overall computer system. Other types of software-controlled general or specific purpose hardware systems may be provided to perform the functions of vision control and processing computer system 302. Hardware not requiring software control, such as logic and/or analog circuitry, may be provided as well.

By way of example, the vision control and processing computer system 302 may be implemented with a VME bus-based vision system, such as a Cognex 5400.

While the images referred to throughout the above disclosure have been monochrome or simple digital images, they may alternatively comprise color information.

While the invention has been described by way of example embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

What is claimed is:

1. A method for detecting an object located within a semi-opaque enclosure having a semi-opaque first side portion having first internal and external surfaces and a semi-opaque second side portion having second internal and external surfaces, said first side portion being different from and opposing said second side portion, said first external surface having a pattern visible externally to said enclosure, said object being located between said first and second side portions, said method comprising:

directing first channel light toward and onto said first external surface of said semi-opaque enclosure;

capturing, from portions of said first channel light reflected off said first external surface but not having passed through said first internal surface, a first digital image comprising data representing said pattern;

directing second channel light toward and onto said object and toward and onto said first side portion of said enclosure;

capturing, from portions of said second channel light emanating from said first external surface after first traveling along side and around said object inside said enclosure and passing through said first internal surface, a second digital image comprising a silhouette of said object; and forming a difference image representing the object and substantially devoid of information representing said visible pattern by subtracting one of said first and second digital images from the other.

2. The method according to claim 1, further comprising generating said first channel light with front lighting.

3. The method according to claim 2, further comprising generating said second channel light with back lighting.

4. The method according to claim 1, further comprising generating said first channel light by directing first light from a location external said enclosure toward and onto said first external surface, whereby said first light hits said first external surface before passing through said first internal surface, said first light being generally orthogonal to said first external surface.

5. The method according to claim 4, further comprising generating said second channel light by directing second light from a location external said enclosure toward and onto said second external surface, whereby said second light hits said second external surface before passing through said second internal surface, said second light being generally orthogonal to said second external surface.

6. A method for detecting an object of unknown shape, configuration, and location on an inner wall surface of a rigid semi-opaque enclosure having a semi-opaque first side portion having first internal and external surfaces and a semi-opaque second side portion having second internal and external surfaces, said first side portion being different from and opposing said second side portion, said first external surface having a pattern visible externally to said enclosure, said method comprising:

directing first channel light toward and onto said first external surface of said semi-opaque enclosure;

capturing, from portions of said first channel light reflected off said first external surface but not having passed through said first internal surface, a first digital image comprising data representing said pattern;

directing second channel light toward and onto said object and toward and onto said first side portion of said enclosure;

capturing, from portions of said second channel light emanating from said first external surface after first traveling along side and around said object inside said enclosure and then passing through said first internal surface, a second digital image comprising a silhouette of said object; and forming a difference image representing said object and substantially devoid of information representing said visible pattern by subtracting one of said first and second digital images from the other.

7. The method according to claim 6, wherein said rigid semi-opaque enclosure comprises a bottle and a semi-opaque label attached to and covering a substantial portion of an outer side-wall surface of said bottle, said substantial portion of said outer side-wall surface including said first external surface.

8. The method according to claim 7, further comprising generating said first channel light with front lighting.

9. The method according to claim 8, further comprising generating said second channel light with back lighting.

10. The method according to claim 7, further comprising generating said first channel light by directing first light from a location external said enclosure toward and onto said first external surface, whereby said first light hits said first external surface before passing through said first internal surface, said first light being generally orthogonal to said first external surface.

11. The method according to claim 10, further comprising generating said second channel light by directing second light from a location external said enclosure toward and onto said second external surface, whereby said second light hits said second external surface before passing through said second internal surface, said second light being generally orthogonal to said second external surface.

12. The method according to claim 10, further comprising generating said second channel light with back lighting.

13. The method according to claim 7, further comprising generating said second channel light by directing second light from a location external said enclosure toward and onto said second external surface, whereby said second light hits said second external surface before passing through said second internal surface, said second light being generally orthogonal to said second external surface.

14. The method according to claim 7, wherein said step of forming a difference image comprises subtracting said second digital image from said first digital image.

15. The method according to claim 7, wherein said first and second digital images comprise two-dimensional gray level images represented with respective two-dimensional light intensity function $f_1(x, y)$ and $f_2(x, y)$, wherein x and y denote spatial coordinates and $f_1$ and $f_2$ are values proportional to the gray level of the respective image at a point x, y.

16. The method according to claim 15, wherein said different image comprises a two-dimensional gray level image, said method further comprising performing a resegmentation operation on said difference image, said resegmentation operation comprising forming a two-dimensional binary image from said difference image.

17. The method according to claim 16, wherein said forming of a two-dimensional binary image from said difference image comprises performing a thresholding operation on said difference image, said thresholding operation comprising forming a two-dimensional binary thresholded image g (x, y) in accordance with the following:

$$g(x, y) = \begin{cases} 1 & \text{if } d(x, y) > p(x, y) \\ 0 & \text{if } d(x, y) \leq p(x, y) \end{cases}$$

where x and y are spatial coordinates of a point (x, y) of said difference image, d (x, y) is the gray level of said point (x, y), and p (x, y) is a local threshold control variable corresponding to said point (x, y).

18. The method according to claim 17, wherein p (x, y) represents a gray level local threshold image defined as a function of at least one of said first and second digital images $f_1(x, y)$ and $f_2(x, y)$.

19. A system for detecting an object of unknown shape, configuration, and location within a semi-opaque enclosure having a semi-opaque first side portion having first internal and external surfaces and a semi-opaque second side portion having second internal and external surfaces, said first side portion being different from and opposing said second side portion, said first external surface having a pattern visible externally to said enclosure, said object being located between said first and said second side portions, said system comprising:

a first light director directing first channel light toward and onto said first external surface of said enclosure;

a first image acquisition subsystem capturing, from portions of said first channel light reflected off said first external surface but not having passed through said first internal surface, a first digital image comprising data representing said pattern;

a second light director directing second channel light toward and onto said object and said first side portion of said enclosure;

a second image acquisition subsystem capturing, from portions of said channel light emanating from said first external surface after first traveling along side and around said object inside said enclosure and then passing through said first internal surface, a second digital image comprising a silhouette of said object; and a processor for forming a difference image representing said object and substantially devoid of information representing said visible pattern by subtracting one of said first and second digital images from the other.

20. The system according to claim 19, wherein said rigid semi-opaque enclosure comprises a bottle and a semi-opaque label attached to and covering a substantial portion of an outer side-wall surface of said bottle, said substantial portion of said outer side-wall surface including said first external surface.

21. The system according to claim 20, wherein said first light director comprises a front light for generating said first channel light.

22. The system according to claim 20, wherein said first light director comprises a first light directed from a location external said enclosure toward and onto said first external surface, whereby said first light hits said first external surface before passing through said first internal surface, said first light directing light in a direction generally orthogonal to said first external surface.

23. The system according to claim 21, wherein said second light director comprises a back light generating said second channel light.

24. The system according to claim 22, wherein said second light director comprises a second light directed from a location external said enclosure toward and onto said second external surface, whereby said second light hits said second external surface before passing through said second internal surface, said second light directing light generally orthogonal to said second external surface.

25. The system according to claim 20, further comprising a vision control and processing computer system, said processor being included in said vision control and processing computer system.

26. The system according to claim 25, wherein said vision control and processing computer system comprises a central processing unit, at least one co-processor, a computer memory device, and an image digitizing device.

* * * * *